United States Patent [19]

Ecke, Jr.

[11] Plant 4,938

[45] Nov. 9, 1982

[54] POINSETTIA NAMED V-14 WHITE

[75] Inventor: Paul Ecke, Jr., Encinitas, Calif.

[73] Assignee: Paul Ecke Ranch, Encinitas, Calif.

[21] Appl. No.: 255,822

[22] Filed: Apr. 20, 1981

[51] Int. Cl.[3] ..... A01H 5/00
[52] U.S. Cl. ..... Plt./86
[58] Field of Search ..... Plt./86

*Primary Examiner*—Robert E. Bagwill
*Attorney, Agent, or Firm*—Chas. W. Rummler

[57] ABSTRACT

A new white poinsettia cultivar orginated as a mutation of V-14 Pink (application Ser. No. 185,121 filed Sept. 5, 1980 and now U.S. Plant Pat. No. 4,808 and having substantially the same physical characteristics and habits as the parent plant.

2 Drawing Figures

BACKGROUND OF THE NEW PLANT

This new poinsettia variety was discovered by me in the beginning of 1980 at my growing and breeding facilities at Encinitas, Calif., this mutation appearing as a branch of the parent plant growing among other branches having heads of the V-14 Pink coloring. This mutation was reproduced by me at Encinitas, Calif., by means of cuttings and such propagation was carried on under my direction to such an extent as to demonstrate clearly that its novel color characteristics were fixed and would hold true from generation to generation.

DESCRIPTION OF THE DRAWINGS

This new poinsettia mutation is shown in the accompanying full color photographic drawings, in which the lower view shows a full face of the mutation as it appeared on the parent plant and the upper view shows the same in side elevation.

DESCRIPTION OF THE NEW PLANT

The following is a general description of this mutation, its physical characteristics and habits, except for color, being practically identical with those of its parent V-14 Pink and its grandparent V-14 Glory (U.S. Plant Pat. No. 4,384). The color designations are according to The R.H.S. Colour Chart published by The Royal Horticultural Society of London, England.

THE PLANT

Origin: Mutation.
Parentage: V-14 Pink (U.S. Plant Pat. No. 4,808).
Classification:
*Botanic.*—*Euphorbia pulcherrima.*
*Commercial.*—Greenhouse poinsettia.
Form: Shrub.
Height: Medium.
Growth habit:

*As a branched plant.*—Upright with very many stems producing a bushy, full appearance.
*As a single stem.*—Upright and vigorous with self-branching side shoots.

Growth rate: Very fast, rooting occurring in about 10 to 15 days under appropriate environment with the plant blooming in about 9 to 10 weeks.

Foliage: Alternate and horizontal, with medium persistence and in normal abundance.
*Leaf size.*—Medium. 4 to 6 inches in length and about 2½ to 4½ inches wide.
*Leaf shape.*—Substantially ovate, with most leaves having one or two serrations on each side.
*Aspect.*—Upper side — Dull with indented veins. Under side — Dull with ordinary veining.
*Color.*—Upper side — Between R.H.S. 137A and 147A. Under side — Close to 137C.
*Retention.*—The foliage lasts well when kept at a low room temperature and with good light intensity.

Bracts: Very many with overlapping arrangement and with a tight center.
*Size.*—Various. Up to about 10 inches long and 6 inches wide.
*Shape.*—Ovate-acuminate with substantially entire margins.
*Petioles.*—From about ¼ inch to about 1 inch in length.
*Color.*—Upper side and under side — Very close to R.H.S. 160C.
*Retention.*—The bract persistence is medium.

I claim:

1. A new and distinctive poinsettia cultivar, substantially as herein shown and described, distinguished by its many bracts of solid white color in overlapping arrangement and tightly centered about the flower cluster; this plant having substantially the identical physical characteristics and growth habits of its parent plant.

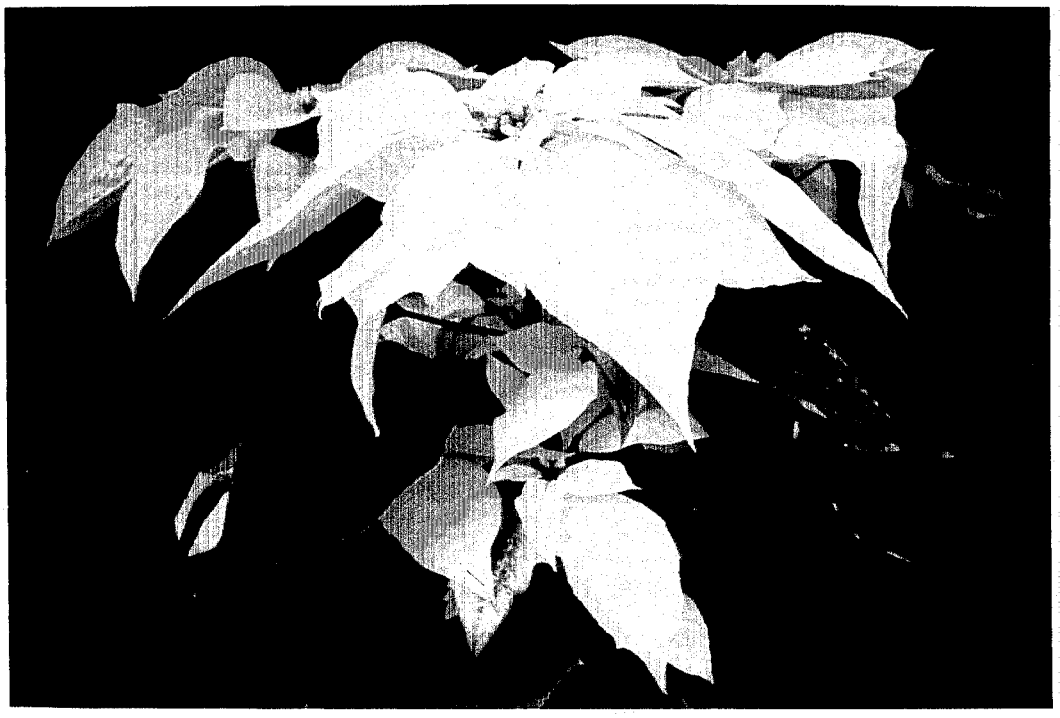
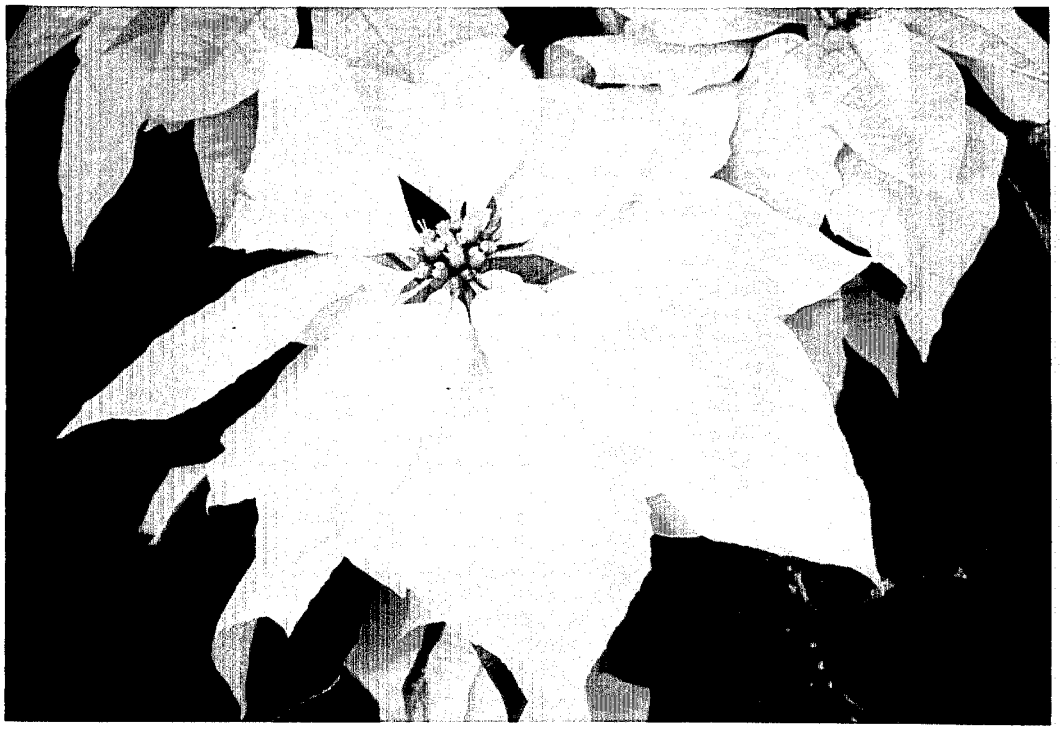

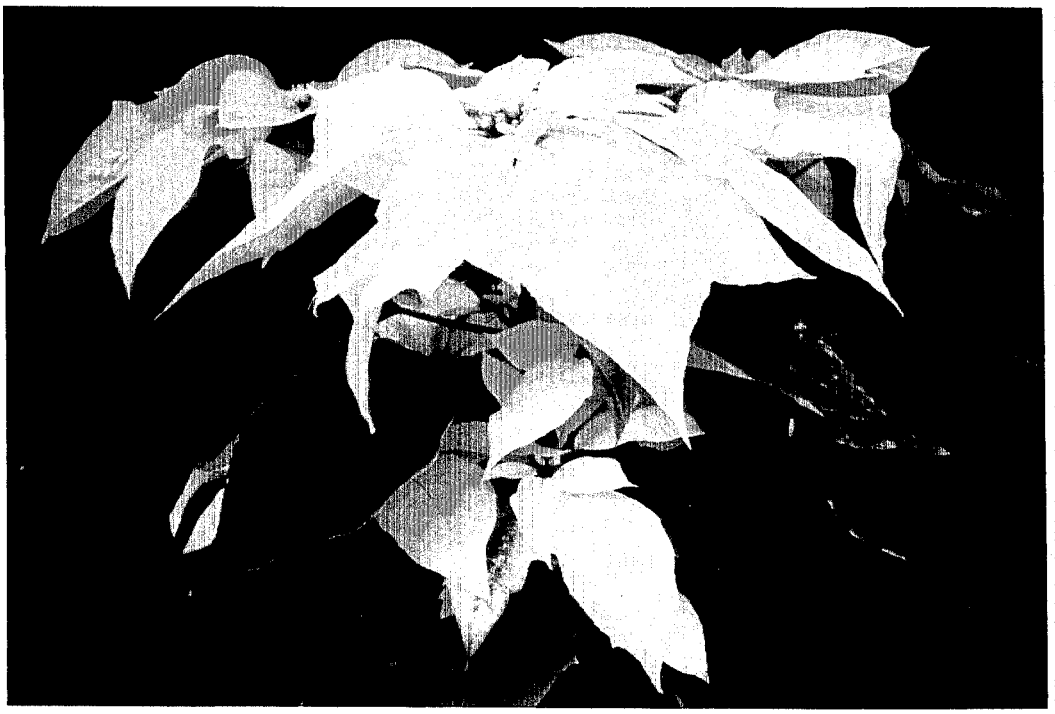
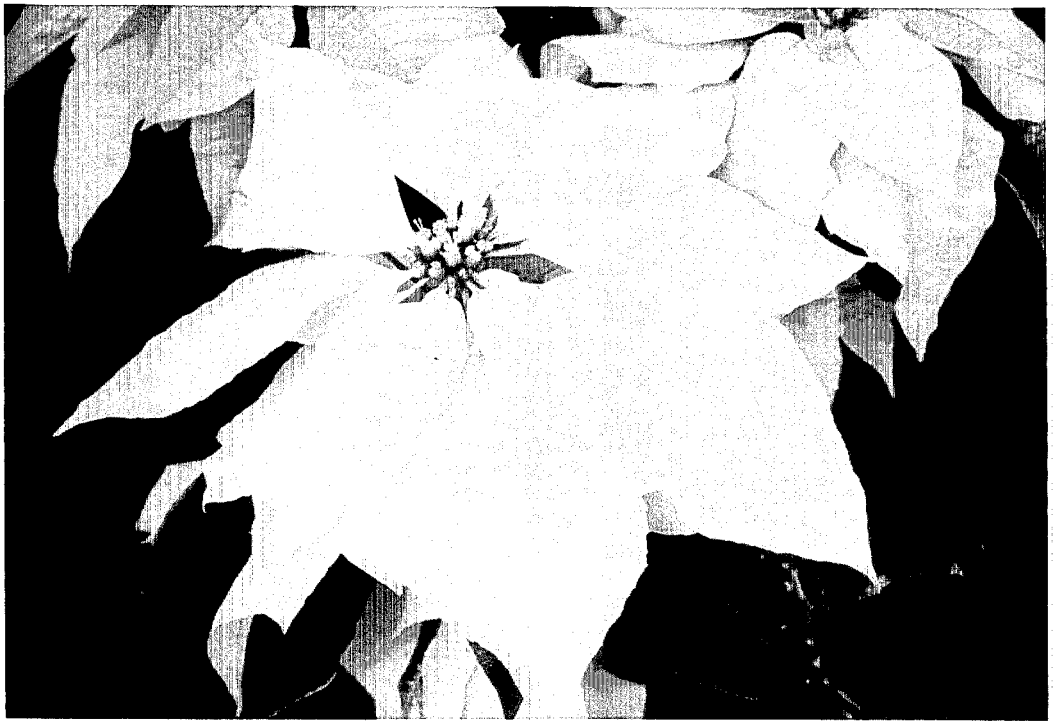

* * * * *